United States Patent [19]

DePalma et al.

[11] 4,120,585
[45] Oct. 17, 1978

[54] FINGERPRINT IDENTIFICATION SYSTEM USING A PLIABLE OPTICAL PRISM

[75] Inventors: Vito A. DePalma, Tonawanda; Raymond W. King, Buffalo, both of N.Y.

[73] Assignee: Calspan Corporation, Buffalo, N.Y.

[21] Appl. No.: 743,424

[22] Filed: Nov. 19, 1976

[51] Int. Cl.² ............................................. G06K 9/08
[52] U.S. Cl. ................................... 356/71; 350/286
[58] Field of Search ................. 356/71; 350/286, 287; 264/1; 340/146.3 E

[56] References Cited
U.S. PATENT DOCUMENTS

| | | | |
|---|---|---|---|
| 3,382,755 | 5/1968 | Papke | 350/286 |
| 3,527,535 | 9/1970 | Monroe | 356/71 |
| 3,532,426 | 10/1970 | Lemmond | 356/71 |
| 3,865,488 | 2/1975 | Del Rio | 356/71 |

*Primary Examiner*—Vincent P. McGraw
*Attorney, Agent, or Firm*—Allen J. Jaffe; David J. Zobkiw

[57] ABSTRACT

A pliable optical prism for use in an optical imaging system such as a fingerprint reader where the prism is physically contacted and the nature of the contact determines the efficiency of the device. The pliable prism deforms under applied pressure to partially mirror the topographic configuration of the source of applied pressure.

3 Claims, 4 Drawing Figures

FINGERPRINT IDENTIFICATION SYSTEM USING A PLIABLE OPTICAL PRISM

Most fingerprint identification systems include an optical element such as a prism which is directly contacted by a finger, or fingers, of the person to be identified. By the proper use of the phenomenon of total internal reflection as applied to a prism, the ridge-valley patterns of a fingerprint can produce a high contrast fingerprint image when viewed at the proper angle. This is true because the light is absorbed where the prism is contacted by the ridges of the finger and reflected where there is no contact. The dimensions of the air gap are not a factor and therefore an air gap of any dimension produces reflection. The quality of the image can be influenced by a number of factors such as dry skin, cuts, creases and new skin. These factors can be overcome in part by a good contact of the finger with the prism and this has been achieved through moderate finger pressure on the prism. While pressure will produce the desired contact with the prism face, it can also introduce a variable amount of distortion as a result of the applied pressure.

Deformable optical elements are known in the prior art as evidenced by U.S. Pat. Nos. 2,300,251 and 2,836,101 which employ fluid pressure to change the configuration of optical elements. When a pliable prism is used as the imaging prism in a fingerprint reader in place of a conventional glass prism, wider ridges result which allow better discrimination of details within the fingerprints of previously difficult-to-analyze fingers. This result of high resolution fingerprints is achieved at a finger pressure much less than would be required for a glass prism to produce comparable results and therefore there is less distortion. Alternatively, if distortion is standardized through the application of a uniform pressure level, uniformly high resolution prints will result due to a positive requirement for sufficient finger pressure by the person to be identified.

It is an object of this invention to provide an optical element which deforms in response to applied pressure to increase its area of contact with the force producing agent.

It is a further object of this invention to provide an optical element suitable for use in a fingerprint identification system and which allows more intimate contact with the finger by yielding under slight pressure.

It is a still further object of the invention to provide an optical element which is capable of producing a fingerprint pattern which more closely resembles the actual fingerprint since it is not necessary to push the finger to distortion to achieve the necessary intimate contact.

It is a yet still further object of this invention to provide an optical element which is pressure deformable to change its optical characteristics.

It is an additional object of this invention to provide an optical system requiring a predetermined degree of physical contact for operation. These objects, and others as will become apparent hereinafter, are accomplished by the present invention.

Basically, the present invention is made up of an optical element which deforms to increase its contact area with a finger in response to pressure and returns to its original shape when the pressure is removed. In addition, the deformable optical element may be provided with a pressure responsive transducer such as a strain gage or a fiducial mark which coacts with a photosensitive element to indicate proper level of finger pressure.

BRIEF DESCRIPTION OF THE DRAWINGS

For a fuller understanding of the present invention, reference should now be had to the following detailed description thereof taken in conjunction with the accompanying drawings wherein.

DESCRIPTION OF THE PREFERRED EMBODIMENTS

The basic techniques used in making a pliable prism are simple since they only involve the use of a suitable pattern or mold and a suitable transparent material to form the prism. If desired, a fiducial spot, transducer, etc. may be either molded into the prism or secured thereto after curing. A suitable prism can be made by filling the mold with a catalyzed mixture of Sylgard 184 which is a clear potting compound manufactured by Dow Corning. The filled mold can then be set in an oven at 90° C. for two hours in order to accelerate the curing of the compound. The index of refraction for such a prism of cured Sylgard 184 is measured to be $1.412n_D$.

Figure 1:
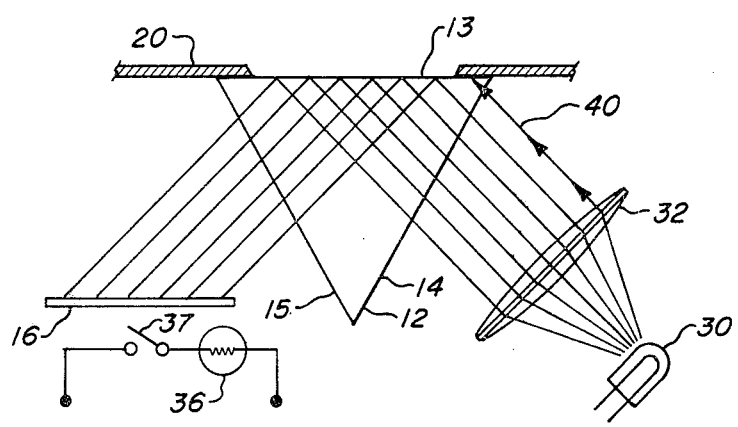
FIGS. 1 and 2 are schematic diagrams of a system incorporating a pliable prism in the ready and operating positions, respectively.

As is best shown in FIG. 1, the pliable prism 12 is normally made up of several planar surfaces. Prism 12 is secured in position by any suitable means such that face 13 of prism 12 is flush against the inner surface of fingerprint terminal housing 20 and at least a part of the area of the prism 12 which is contacted by the housing 20 is free to deform under pressure from a contacting finger. Light from light source 30 passes through collimating lens 32 through face 14 of prism 12 and through prism 12 to prism face 13. Due to the phenomenon of total internal reflection, light striking prism face 13 will be reflected internally wherever prism face 13 is not in physical contact with another member. Where prism face 13 is in contact with housing 20, the light will be absorbed, such as beam 40 but where there is a prism — air interface the light will be reflected internally at face 13 through prism 12 and out through face 15 onto element 16 which may be a screen, photosensitive device etc. depending upon the system. A photosensitive device 36 is in a circuit which is schematically represented by open switch 37 for actuating the system.

OPERATION

Figure 2:
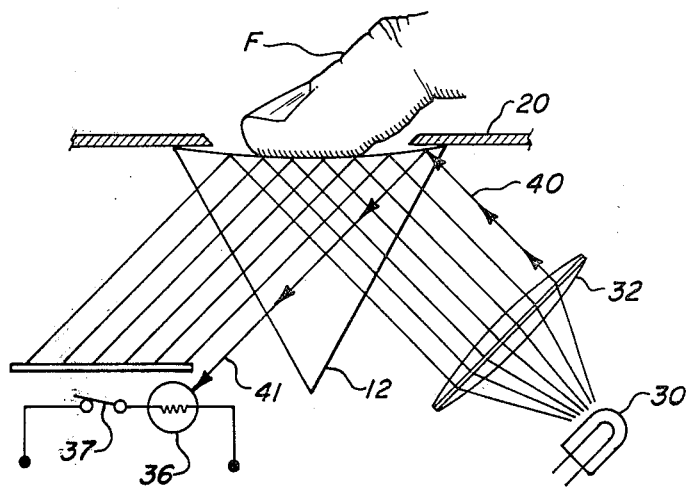
Figure 3:
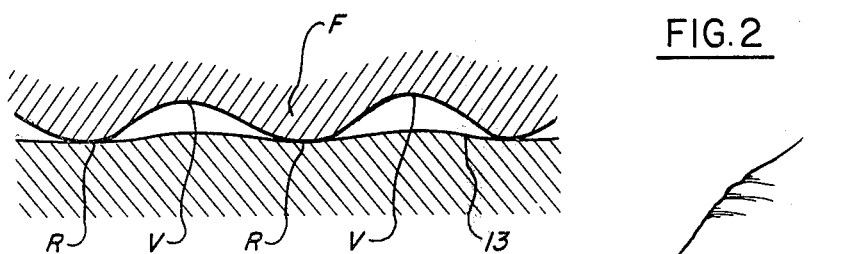
FIG. 3 is an exaggerated sectional view of the finger-prism interface.

As shown in FIG. 2, when a finger F is placed on face 13 of pliable prism 12, pressure exerted by the finger F causes a deformation of face 13 of the pliable prism 12 which results in the creating of an air gap between prism face 13 and housing 20. The presence of the air gap results in internal reflection from portions of prism face 13 at which absorption took place in the FIG. 1 position, such as reflected beam 41. By the proper placing of photosensitive device 36 reflection from the additional reflecting area, the fiducial spot, light beam 40 and resulting reflected beam 41 activate photosensitive device 36 to cause the activation of the terminal as indicated by the closing of switch 37. Thus there is a positive requirement for sufficient finger pressure to activate the system. FIG. 3 clearly shows that prism face 13 partially mirrors the ridge-valley pattern of finger F to present a broader absorption area for each ridge due to the greater area of contact at the interface of finger F and face 13. Although FIG. 3 shows a rippled surface 13 acting as a mirror, the amount of topographic relief is very small since the prism 12 would not be operative if capable of extruding into and filling the valleys V of finger F. There is, of course, a scattering of light due to the irregular surface 13, but the small amount of topographic relief and greater contact area with the ridges R give a net gain over conventional rigid optical elements.

Figure 4:
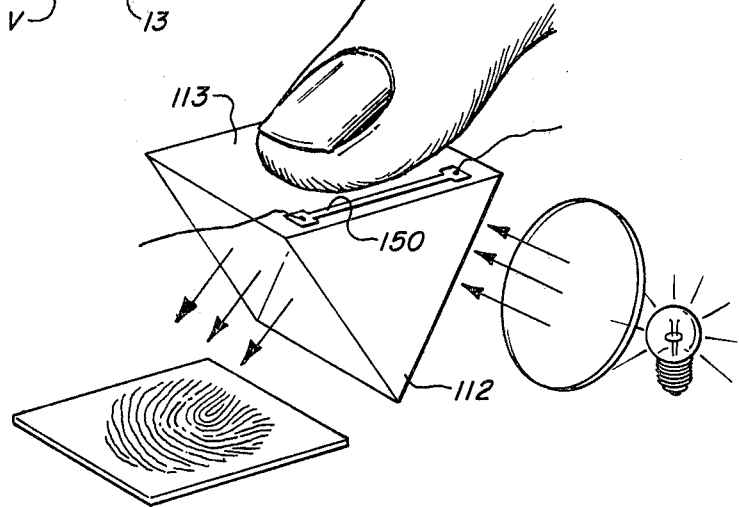
FIG. 4 is a perspective view of a modified prism.

The system of FIG. 4 would be similar in operation to the system of FIGS. 1 and 2. The basic difference is in the providing of one or more strain gages 150, or other transducer elements, which are located in a system actuating circuit (not illustrated). In response to applied pressure on face 113 of prism 112, the strain gage 150 will be stressed and will cause the actuation of the system.

Although the fiducial spot has been illustrated as the location of the air gap produced by sufficient finger pressure, it may also be an absorbing or reflecting area in or on the prism which is displaced due to finger pressure to cause a reflected light to move onto or off a photosensitive device. The prism may also have incorporated therein or located thereon a triggering edge which is a reference location on the finger contacted face for use in analyzing data and is a sharply defined absorption area. While a prism having a cross section of an equilateral triangle has been illustrated, other geometric cross sections can be employed. The prism has been described as made of Sylgard 184 but it may be made of any clear polymeric material which is pliable when cured.

Although preferred embodiments of the present invention have been illustrated and described, other changes will occur to those skilled in the art. It is therefore intended that the scope of the present invention is to be limited only by the scope of the appended claims.

We claim:

1. A fingerprint based identification terminal including:
    sensor means;
    optically clear, pliable, resilient prism means;
    light source means for shining onto one internal surface of said prism means and being internally reflected onto said sensor means in accordance with the topographic configuration of any member contacting the external surface corresponding to said one internal surface and any resulting deformation of said one internal surface;
    whereby when a finger contacts a planar surface of said prism means corresponding to said one internal surface, said planar surface and thereby said internal surface will deform to partially mirror the ridge-valley configuration of the contacting finger to give a greater area of contact resulting in a high contrast image being reflected onto said sensor means due to absorption of light at said one internal surface where said planar surface is contacted by the finger.

2. The fingerprint based identification terminal of claim 1 further including transducer means for generating an actuating signal to activate said terminal when sufficient pressure is exerted by a finger against said prism means.

3. A fingerprint based identification terminal including:
    first sensor means;
    second sensor means;
    optically clear, pliable and resilient prism means;
    light source means for shining onto one internal surface of said prism means and being internally reflected onto said first sensor means;
    housing means in direct contact with a portion of a planar surface of said prism means corresponding to said one internal surface;
    whereby when a finger contacts said planar surface of said prism means, said planar surface and thereby said internal surface will deform to create an air gap between at least a portion of said prism means and said housing means to cause additional internal reflection of light from said light source means onto said second sensor means to cause the generation of a terminal activating signal and said deformation of said planar and inner surfaces partially mirroring the ridge-valley configuration of the contacting finger to give a greater area of contact resulting in a high contrast image being reflected onto said first sensor means due to absorption of light at said one internal surface where said planar surface is contacted by the finger.

* * * * *